(12) United States Patent
Bruce et al.

(10) Patent No.: US 7,416,897 B2
(45) Date of Patent: Aug. 26, 2008

(54) METHOD FOR HIGH-THROUGHPUT SCREENING ASSAY SAMPLE PREPARATION AND ANALYSIS

(75) Inventors: Richard H. Bruce, Los Altos, CA (US); Francisco E. Torres, San Jose, CA (US); Alan G. Bell, Palo Alto, CA (US); Eric Peeters, Fremont, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 780 days.

(21) Appl. No.: 10/719,961

(22) Filed: Nov. 21, 2003

(65) Prior Publication Data

US 2005/0112766 A1    May 26, 2005

(51) Int. Cl.
*G01K 17/00* (2006.01)
*G01K 17/20* (2006.01)
*G01N 35/00* (2006.01)
*G01N 25/20* (2006.01)

(52) U.S. Cl. .................. 436/147; 422/50; 422/51; 422/68.1; 422/82.12; 436/43; 436/174; 436/175; 436/180; 374/31; 374/32

(58) Field of Classification Search .................. 422/50, 422/68.1, 51, 82.12; 436/147, 180, 174, 436/175, 43; 374/31, 32
See application file for complete search history.

(56) References Cited

U.S. PATENT DOCUMENTS

| | | | | |
|---|---|---|---|---|
| 5,942,443 A | 8/1999 | Parce et al. | .................. | 436/514 |
| 6,294,063 B1 * | 9/2001 | Becker et al. | ................ | 204/450 |
| 6,380,605 B1 | 4/2002 | Verhaegen | .................. | 257/467 |
| 6,545,334 B2 | 4/2003 | Verhaegen | .................. | 257/467 |
| 2004/0038227 A1 * | 2/2004 | Verwaerde et al. | ............. | 435/6 |
| 2005/0076943 A1 * | 4/2005 | Cooper et al. | ................ | 136/224 |

OTHER PUBLICATIONS

Lehto et al. (WO 99/54730).*
U.S. Appl. No. 09/946,047, filed Sep. 4, 2001, Connelly et al.
U.S. Appl. No. 10/114,611, filed Apr. 1, 2002, Bell et al.
U.S. Appl. No. 10/115,336, filed Apr. 1, 2002, Elrod et al.
U.S. Appl. No. 10/159,606, filed May 31, 2002, Chow et al.
U.S. Appl. No. 10/303,446, filed Nov. 22, 2002, Bruce et al.
U.S. Appl. No. 10/303,500, filed Nov. 22, 2002, Bruce et al.
R. Seethala, P.B. Fernandes, eds, Handbook of Drug Screening, Marcel Dekker Inc., 2001.

* cited by examiner

*Primary Examiner*—Brian J Sines
(74) *Attorney, Agent, or Firm*—Fay Sharpe LLP

(57) ABSTRACT

A method is disclosed for high-throughput screening assay sample preparation and testing for the identification of binding between drug targets and library compounds, for use with a calorimetric device measuring the enthalpy of reaction for the binding. The method includes mixing a library compound with a specified solvent and mixing a target compound solution with a second specified solvent on a calorimetric device. The library compound/solvent is merged with the target compound/solvent solution and the library compound/solvent solution is also merged with a third solvent solution on the calorimetric device. The heats of reaction are detected for both merged solutions and are compared.

31 Claims, 6 Drawing Sheets

METHOD FOR HIGH-THROUGHPUT SCREENING ASSAY SAMPLE PREPARATION AND ANALYSIS

CROSS-REFERENCE TO RELATED APPLICATIONS

The following co-pending applications, U.S. application Ser. No. 10/114,611, filed Apr. 1, 2002, titled "Apparatus and Method for a Nanocalorimeter for Detecting Chemical Reactions"; U.S. application Ser. No. 10/115,336, filed Apr. 1, 2002, titled "Apparatus and Method for Using Electrostatic Force to Cause Fluid Movement"; U.S. application Ser. No. 10/303,446, filed Nov. 22, 2002, titled "Apparatus and Method for Lead Profiling Assay"; and U.S. application Ser. No. 10/303,500, filed Nov. 22, 2002, titled "Apparatus and Method for Multiple Target Assay for Drug Discovery", are assigned to the same assignee of the present application. The entire disclosures of these applications are totally incorporated herein by reference in their entirety.

INCORPORATION BY REFERENCE

The following U.S. patents and patent applications are fully incorporated herein by reference: U.S. Pat. No. 5,942,443 to Parce et al. ("High Throughput Screening assay Systems in Microscale fluidic Devices"); U.S. Pat. No. 6,380,605 to Verhaegen ("Device and a Method for Thermal Sensing"); U.S. Pat. No. 6,545,334 to Verhaegen ("Device and a Method for Thermal Sensing"); U.S. application Ser. No. 10/159,606 to Chow et al. ("Microfluidic Library Analysis"); and U.S. application Ser. No. 09/946,047 to Connelly et al. ("Drug Discovery Employing Calorimetric Target Triage").

BACKGROUND

This disclosure relates generally to methods for sample preparation and analysis utilized within high-throughput screening assays. More specifically, the method is directed at improvements in regulating sample composition for screening assays for use within a nanocalorimeter.

In recent years, researchers and companies have turned to combinatorial methods and techniques for synthesizing, discovering and developing new compounds, materials, and chemistries. For example, pharmaceutical researchers have turned to combinatorial libraries as sources of new lead compounds for drug discovery. Consequently, there is a need for tools that can measure reactions and interactions of large numbers of small samples at high rates, consistent with the needs of combinatorial discovery techniques. Preferably, users desire that these tools enable quick, inexpensive measurements and minimize contamination and cross-contamination problems. In addition there has been an explosion in the number of potential drug targets due to the accelerated implementation of genomics technologies and the completion of the Human Genome sequence.

To further illustrate the use of combinatorial chemistry methods and the need for improved methods, we now discuss the example of pharmaceutical research in this area in more detail. Pharmaceutical researchers have turned to combinatorial libraries as sources of new lead compounds for drug discovery. A combinatorial library is a collection of chemical compounds that have been generated, by either chemical synthesis or biological synthesis, by combining a number of chemical "building blocks" as reagents. For example, a combinatorial polypeptide library is formed by combining a set of amino acids in every possible way for a given compound length (i.e., the number of amino acids in a polypeptide compound). Millions of chemical compounds can theoretically be synthesized through such combinatorial mixing of chemical building blocks.

Once a library has been constructed, it must be screened to identify compounds, which possess some kind of biological or pharmacological activity. For example, screening can be done with a specific biological molecule, often referred to as a target molecule that participates in a known biological pathway or is involved in some regulatory function. The library compounds that are found to react with the targets are candidates for affecting the biological activity of the target, and hence a candidate for a therapeutic agent.

Since combinatorial methods involve looking at a large number of compounds and reactions, there is a need for tools that can measure reactions and interactions of large numbers of small samples at an accelerated measurement rate, consistent with the needs of combinatorial discovery techniques. Preferably, users desire that these tools enable inexpensive measurements and minimize contamination and cross-contamination problems.

One method for measuring reactions and interactions is calorimetry. Calorimetry can be used to measure the thermodynamics and kinetics of reactions without requiring that reactants be labeled (e.g., radio-labeled or labeled with fluorophores) or immobilized on surfaces. Most other current methods require some modification of either the substrate or a cofactor (fluorescent labeling, surface anchoring, etc.) [*Handbook of Drug Screening*, R. Seethala and P. B. Fernandes, eds., Marcel Dekker Inc., 2001]. These modifications add steps and cost to an assay, and unless considerable effort is expended to develop a non-interfering assay, they can potentially modify the reagents in undesired ways that may not be understood at the time of an assay.

In some cases, the sample to be studied is precious, and it might not be acceptable to use the relatively large amount of material required by a standard microcalorimeter to perform only one measurement. For example, one may desire to study a natural extract or synthesized compound for biological interactions, but in some cases the available amount of material at concentrations large enough for calorimetry might be no more than a few milliliters. Performing a measurement in standard microcalorimeters, such as those sold, for example, by MicroCal® Inc. (model VP-ITC) or Calorimetry Sciences Corporation® (model CSC-4500), requires about 1 ml of sample, which means that one would possibly be faced with using a majority or all of the precious material for one or a small series of measurements. Tools that enable calorimetric measurements with much smaller sample sizes would be helpful in overcoming this limitation.

A variety of measurement approaches has been used to screen combinatorial libraries for lead compounds, one of which is the competitive binding assay. In this assay, a marker ligand, often the natural ligand in a biological pathway, is identified that will bind well with the target molecule. The assay often requires the chemical attachment of a fluorescent molecule to this marker ligand, and it is important that the fluorescent molecule does not affect the manner in which the marker ligand reacts with the target molecule. Alternatively, the ligand could be radioactively labeled or labeled with a chemiluminescent molecule.

To provide an illustrative example, one approach to operating a competitive binding assay utilizes a target molecule, which is exposed to a mixture of test ligands and a marker ligand, often in microtitre wells. After a time for reaction, the wells are rinsed such that free marker ligand is washed away. In wells where the target molecule and the test ligand are strongly bound relative to binding of the marker ligand, the test ligand has blocked the active site of the target molecule so the marker ligand is not bound and is washed away. Conversely, in wells where the target molecule and test ligand do not bind strongly relative to binding of the marker ligand, the marker ligand binds to the target molecule, at least to some extent, and is therefore not washed away. By investigating the wells for the presence of fluorescence after the washing, reactions of test ligands and target molecules can be determined as having occurred in wells where reduced fluorescence is observable relative to control wells to which no test ligands have been added.

However, competitive binding assays require time and expense to develop the labeled reagents and assay. The principal components that need development are discovering a marker ligand and attaching a fluorophore to the marker in a manner that does not affect its reaction with the target molecule. Attaching the fluorescent marker can often take 3 months of development or more and cost $250K or more once the marker ligand is identified.

An alternative approach is described in U.S. application Ser. No. 10/114,611, filed Apr. 1, 2002, titled "Apparatus and Method for a Nanocalorimeter for Detecting Chemical Reactions". In this approach, two drops, each containing different reactants, are merged together, and the resulting heat evolution is detected. The signal is detected relative to a reference signal, resulting in detection of the net heat of reaction. However, this approach requires that the two drops have a similar composition, or that the dissimilarities in composition are matched in the reacting drops and the reference system, to keep the heat of mixing from obscuring the heat of reaction. The common mode rejection realized from comparison of the reference and measurement reactions will substantially reduce the contribution of heats of mixing when reference and measurement reactions are well matched. However, problems arise in preparing the necessary solutions to have similar compositions for the purposes of minimizing heats of mixing effects. Since the reactants may have different solvents and co-solvent concentrations when being synthesized and stored, an expensive mixing step and complicated drop-dispensing step are required. An assay method that eliminates the intermediate mixing step required for control of solution composition and simplifies drop dispensing would eliminate this cost and time delay in the discovery process.

Yet another problem is the complexity associated with depositing many different compounds from a compound library at the time of measurement. Since the number of compounds can be large, the control of the delivery of compounds and the need to clean any tips or needles when switching from one compound to another complicates the delivery of reagents to an array such as a nanocalorimeter array. A method that enables pre-formatting of arrays prior to their use and reduces the number of different solutions that need to be delivered or deposited at the time of the measurement would help mitigate this problem.

BRIEF SUMMARY

The disclosed embodiments provide examples of improved solutions to the problems noted in the above Background discussion and the art cited therein. There is shown in these examples an improved method to distribute the chemical libraries, simplification in test measurement, and methods of use, which may provide some or all of the following features.

Briefly described, in one embodiment a method is disclosed for high-throughput screening assay sample preparation and testing for the identification of binding between drug targets and library compounds, for use with a calorimetric device measuring the enthalpy of reaction for the binding. The method includes mixing a library compound with a specified solvent, and also providing a target compound solution with a second specified solvent, on a calorimetric device. The library compound/solvent solution is merged with the target compound solution and a separate sample of the library compound/solvent solution is also merged with a third solvent solution on the calorimetric device. The heats generated upon merging are detected for both merged solutions and are compared.

In another embodiment there is disclosed a method for high-throughput screening assay sample preparation and analysis for use within a nanocalorimeter, in which the nanocalorimeter includes thermal isolation regions, reference regions, and measurement regions. The method includes depositing drops of a first and second solvent solution within reference and measurement regions on the nanocalorimeter, with at least one drop of each being placed in each region. Target compound is deposited with the second solvent solution in the measurement region and the two are mixed to form a target compound/solvent. Selected library compound solution is deposited with the first solvent solution in the measurement and reference regions and is mixed to form a library compound/solvent solution. The library compound/solvent solution is merged with the second solvent solution within the reference region and the heat of reaction is detected. The library compound/solvent solution is merged with the target compound/solvent solution within the measurement region and the heat of reaction is detected. The heats of reaction are then compared.

In yet another embodiment there is disclosed a method for high-throughput screening assay sample preparation and analysis for use within a nanocalorimeter, which includes thermal isolation regions and measurement regions. The method includes depositing target material and selected library compound solution within different locations in the measurement region. The library compound solution is then merged with the target material solution and the heat of reaction is detected and measured.

BRIEF DESCRIPTION OF THE DRAWINGS

The foregoing and other features of the embodiments described herein will be apparent and easily understood from a further reading of the specification, claims and by reference to the accompanying drawings in which:

DETAILED DESCRIPTION

Figure 1:
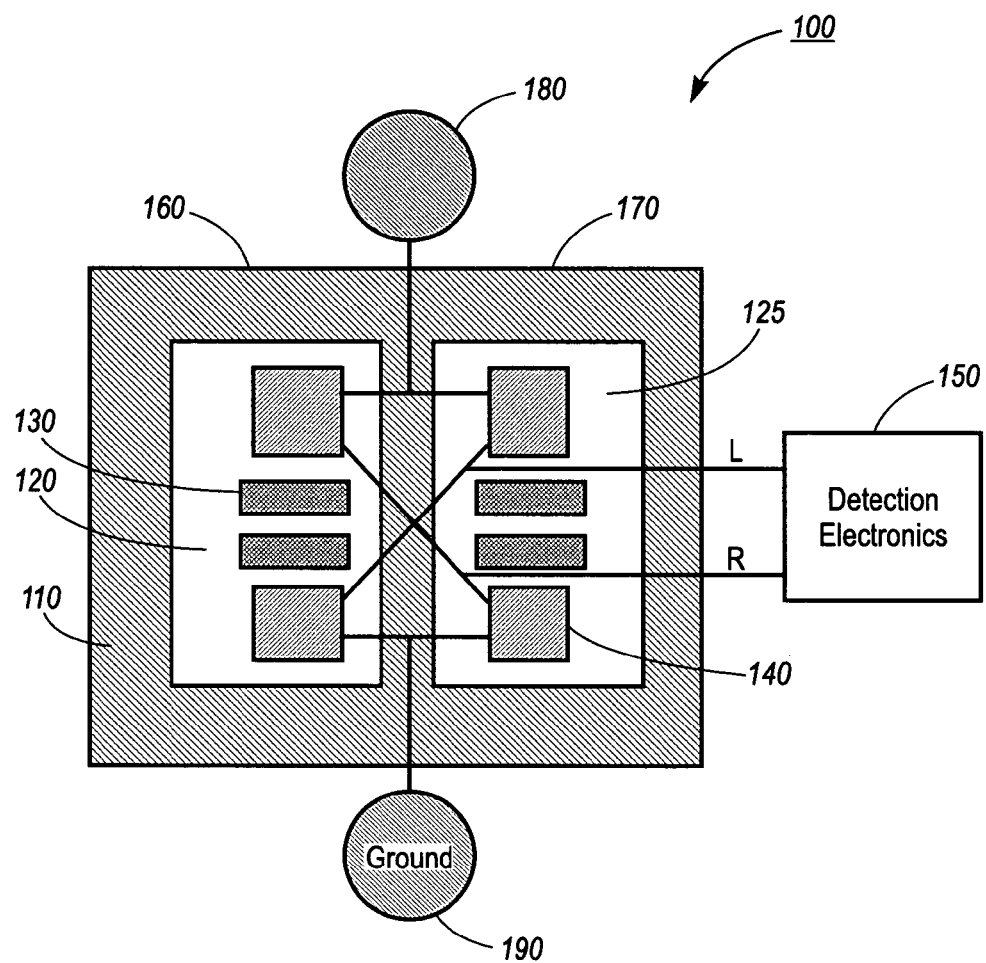
FIG. 1 is a block diagram depicting components of one embodiment of a nanocalorimeter utilized in practicing the method herein.

As used herein, the term "ligand" refers to an agent that binds to a target compound. For the purposes herein, a ligand is not limited to an agent that binds a recognized functional region of the target molecule, e.g., the active site of an enzyme, the antigen-combining site of an antibody, the hormone-binding site of a receptor, a cofactor-binding site, and the like. In practicing the present method, a ligand can also be an agent that binds any surface or conformational domains of the target molecule. Therefore, the ligands of the present method encompass agents that in and of themselves may have no apparent or known biological function, beyond their ability to bind to the target compound in the manner described above.

As used herein, the term "test ligand" refers to an agent, comprising a compound, molecule or complex, which is being tested for its ability to bind to a target compound. Test ligands can be virtually any agent, including without limitation metals, peptides, proteins, lipids, polysaccharides, nucleic acids, small organic molecules, and combinations thereof. Complex mixtures of substances such as natural product extracts, which may include more than one test ligand, can also be tested, and the component that binds the target compound can be purified from the mixture in a subsequent step.

As used herein, "screening" refers to the testing of a multiplicity of molecules or compounds for their ability to bind to a target compound.

As used herein, the term "target compound" encompasses peptides, proteins, nucleic-acids, protein-nucleic acid complexes, and other receptors. The term encompasses both enzymes and proteins that are not enzymes. The term encompasses monomeric and multimeric proteins. Multimeric proteins may be homomeric or heteromeric. The term encompasses nucleic acids comprising at least two nucleotides, such as oligonucleotides. Nucleic acids can be single-stranded, double-stranded, or triple-stranded. The term encompasses a nucleic acid which is a synthetic oligonucleotide, a portion of a recombinant DNA molecule, or a portion of chromosomal DNA, as well as RNA, including mRNA, tRNA, snRNA, rRNA, and cRNA. The term target compound also encompasses portions of peptides, secondary, tertiary, or quaternary structure through folding, with substituents including, but not limited to, cofactors, coenzymes, prosthetic groups, lipids, oligosaccharides, or phosphate groups.

As used herein, the term "thermal change" encompasses the release of energy in the form of heat or the absorption of energy in the form of heat.

As used herein, the term "merging of a target compound" refers broadly to placing the target compound in solution with the molecule to be screened for binding. Less broadly, merging refers to the turning, swirling, shaking or vibrating of a solution of the target compound and the molecule to be screened for binding. More specifically, merging refers to the mixing of the target compound with the molecule to be tested for binding. Mixing can be accomplished, for example, by repeated uptake and discharge through a pipette tip or by deposition by robotic means. Merging may refer to the equilibration of binding between the target compound and the molecule to be tested for binding, which may be accomplished in any of numerous ways. For example, sufficient time may be allowed for mixing by diffusion, or mixing may be the result of drop merging, the application of electrical force, and the like.

As used herein, the term "biochemical conditions" encompasses any component, thermodynamic property, or kinetic property of a physical, chemical, or biochemical reaction. Specifically, the term refers to conditions of temperature, pressure, protein concentration, pH, ionic strength, salt concentration, time, electric current, potential difference, and concentrations of cofactor, coenzyme, oxidizing agents, reducing agents, detergents, metal ion, ligands, buffer components, co-solvents including DMSO (dimethyl sulfoxide), glycerol, and related compounds, enhancers, and inhibitors.

As used herein, the term "high-throughput" refers broadly to investigations with a large number of tests such that formatting of each individual sample, minimizing preparation steps and complications, and measuring of the tests either in parallel or in rapid succession become important. High-throughput tests do not include manual, one-at-a-time tests, such as tests by a single individual in which the preparation, execution, measurement, and data collection for one test are all completed before the test on the next compound (e.g., a second test ligand) is done. High-throughput is meant to include, for example, any tests in which 24, 96, or 384, element arrays are prepared and measured, since formatting the tests in such an array is meant to accelerate the test process by enabling measurement in parallel or in rapid succession, perhaps with the assistance of automation.

The present method encompasses nanocalorimeters and nanocalorimeter arrays that enable measurement of enthalpic changes, such as enthalpic changes arising from reactions, phase changes, changes in molecular conformation, changes in salvation, and the like. For the purposes herein, a nanocalorimeter refers to a device capable of measuring heats of reaction in the range of nanocalories or higher, for example within the range of approximately 0.01 nanocalories to 10000 nanocalories. Furthermore, the present method encompasses combinatorial methods and high-throughput screening methods that use nanocalorimeters in the study, discovery, and development of new compounds, materials, chemistries, and chemical processes, as well as high-throughput monitoring of compounds or materials, or high-throughput monitoring of the processes used to synthesize or modify compounds or materials. The present method also relates to compounds or materials identified by the above methods and their therapeutic uses (for diagnostic, preventive or treatment purposes), uses in purification and separation methods, and uses related to their novel physical or chemical properties.

As an example, the present method encompasses high-throughput screening methods for identifying a ligand that binds a target compound. If the target compound to which the test ligand binds is associated with or causative of a disease or condition, the ligand may be useful for diagnosing, preventing or treating the disease or condition. A ligand identified by the present method can also be one that is used in a purification or separation method, such as a method that results in purification or separation of the target compound from a mixture. The present method also relates to ligands identified by the present method and their therapeutic uses (for diagnostic, preventive or treatment purposes) and uses in purification and separation methods.

In practicing the present method, the test ligand is combined with a target compound, and the mixture is maintained under appropriate conditions and for a sufficient time to allow binding of the test ligand to the target compound, if binding occurs. Experimental conditions are determined empirically for each target compound. When testing multiple test ligands, incubation conditions are usually chosen so that most ligand: target compound interactions would be expected to proceed to completion. In high-throughput screening applications, the test ligand is usually present in molar excess relative to the target compound. The target compound can be in a soluble form, can be in a cell membrane, membrane fragment, synthetic organelle or organelle fragment, micelle or equivalent heterogeneous environment, or, alternatively, can be bound to a solid phase matrix. The matrix may comprise without limitation beads, membrane filters, plastic surfaces, or other suitable solid supports.

Binding to a given target compound is a prerequisite for pharmaceuticals intended to directly modify the action of that target compound. Thus, if a test ligand is shown, through use of the present method, to bind a target compound that reflects or affects the etiology of a condition, it may indicate the potential ability of the test ligand to alter target function and to be an effective pharmaceutical or lead compound for the development of such a pharmaceutical. Alternatively, the ligand may serve as the basis for the construction of hybrid compounds containing an additional component that has the potential to alter the target's function. For example, a known compound that inhibits the activity of a family of related enzymes may be rendered specific to one member of the family by conjugation of the known compound to a ligand, identified by the methods of the present method, that binds specifically to that member at a different site than that recognized by the known compound.

The fact that the present method is based on physicochemical properties common to most targets gives it widespread application. The present method can be applied to large-scale systematic high-throughput procedures that allow a cost-effective screening of many thousands of test ligands. Once a ligand has been identified by the methods of the present method, it can be further analyzed in more detail using known methods specific to the particular target used. Also, the ligand can be tested for its ability to influence, either positively or negatively, a known biological activity of the target compound.

For the purposes of the discussion herein, embodiments of a nanocalorimeter are used to illustrate the operation of the assay sample preparation and analysis method. However, those skilled in the art will readily appreciate that the method may be employed beneficially on other nanocalorimeter configurations as well as microcalorimeter configurations, all of which are fully contemplated by the specification and scope of the claims herein.

Referring now to FIG. 1, there is shown a plan view of one embodiment of detector 100 that is a part of one embodiment of a nanocalorimeter array which may be utilized in accordance with the method herein. This example embodiment enables a passive thermal equilibration of the combined protein, water and ligand drops with the device so that the resultant temperature changes can be detected by means of a temperature sensing device. Because the measurement region is kept small enough and sufficiently thermally conductive, through the fabrication of a thermally conducting layer such as aluminum or copper, the passive equilibration time can be made small. This sample embodiment of a nanocalorimeter is described in more detail in U.S. application Ser. No. 10/114, 611, "Apparatus and Method for a Nanocalorimeter for Detecting Chemical Reactions", incorporated by reference hereinabove.

Some of the features of this embodiment of a nanocalorimeter will be briefly described to facilitate understanding of the method presented herein, but it will be understood that this is only one example embodiment of a suitable nanocalorimeter to be used in practicing the method herein, which may be beneficially applied in various embodiments with various forms of nanocalorimeter, all of which are fully contemplated by the scope of the specification and claims herein. Nanocalorimeter 100 includes thermal isolation layer 110, which contains measurement region 160 and reference region 170. Regions 160 and 170 may also be contained in separate isolation regions, as described hereinbelow. Thermal isolation region 110, and the vapor phase surrounding the measurement and reference regions, provides isolation from surrounding thermal environments, thus increasing measurement time and reducing thermal noise. Although layer 110 is used in this example embodiment to thermally isolate the reaction and temperature sensing components of the nanocalorimeter 100, any means to thermally isolate these components can be used in alternate embodiments of the present method.

Measurement region 160 and reference region 170 include thermal equilibrium regions 120 and 125, respectively, that are thermally isolated from the detector's mechanical support. In this example embodiment, thermal equilibrium region 120 contains two resistive thermometers 140, which measure the reaction temperature, while thermal equilibrium region 125 contains a second set of two thermometers 140, which measure the variations in the background temperature. The resistive thermometers are deposited in thermal equilibrium regions 120 using standard fabrication techniques, including in embodiments, but not limited to, lithographic patterning of thin films, micro-electronic fabrication techniques (e.g., including sputtering, chemical etching, evaporation), and printed circuit board fabrication techniques. Both thermal equilibrium regions 120 and 125 are sufficiently large to receive and support separate drops of protein and ligand deposited by direct printing and also to support the combination of these two drops after merging, triggered by an example drop merging device 130. For example, for a 400 nL final drop size, the detector, which includes the measurement and reference regions, may be 3.7 mm by 4.6 mm. Each thermal equilibration region 120 and 125 has a sufficient thermal conduction for the region to equilibrate quickly relative to the thermal dissipation. In embodiments, this thermal conduction is provided by a high thermal conductance film that spans each region on either side of a support membrane.

As suggested above, the thermal equilibration regions must be thermally isolated from their environment so that the temperature difference caused by the reaction takes a relatively long time to dissipate. The longer this dissipation time, the longer the signal can be integrated during measurement, which improves the signal to noise ratio.

Each thermal equilibration region 120 and 125 contains thermometers 140 and drop merging electrodes 130. Although for the purposes herein thermometers 140 are shown spaced apart from more centrally-positioned drop merging electrodes 130 on each thermal equilibration region 120 and 125, this configuration is for means of example only. Provided that the drop merging device 130 and thermometers 140 are in good thermal contact with the high conductance film, the exact placement of thermometers 140 and drop merging electrodes 130 is not important for thermal considerations.

In operation, the two resistive thermometers 140 situated in thermal equilibration region 120 detect the heat of reaction between an arbitrary target compound and a test ligand deposited within thermal equilibration region 120. In this example, the heat of reaction is detected through measurement of a voltage change in a bridge circuit due to the resistance change in the thermometers, which are configured in the bridge circuit. Resistive thermometers 140 in thermal equilibrium region 120 detect a reaction between a test ligand and a target compound; the other resistive thermometers 145 in thermal equilibrium region 125 serve as a reference.

As an embodiment, the method disclosed herein utilizes nanocalorimetry in the identification of target-ligand pairs. Nanocalorimetry, such as described in U.S. application Ser. No. 10/114,611 ("Apparatus and Method for a Nanocalorimeter for Detecting Chemical Reactions"), is useful for this purpose because it directly detects the heat of reaction upon binding of a ligand to a target. No attachment of tags, such as fluorescent, chemiluminescent, or radio-labeled tags, or other special formatting or immobilization of the ligands or targets is necessary.

Figure 2:
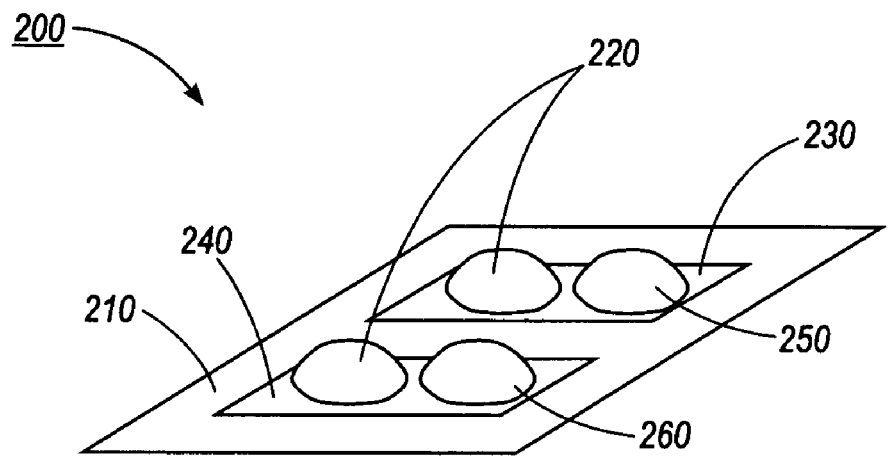
FIG. 2 is an illustration depicting solvent and target drop deposition within a single cell of a testing array, according to one embodiment of the method.

The method disclosed herein provides for the dispensing of drops of solution from higher concentration sources. In drug screening, a large number of library compounds (perhaps as many as 500,000-1,000,000 or more) are screened against specific targets. The compounds are typically stored at high concentrations (perhaps 100 micromolar to 10 millimolar) in a solvent containing water and dimethyl sulfoxide (DMSO), in solution at 50% -100%, while the targets are generally in aqueous buffers. Turning now to FIG. 2, there is shown one embodiment of drop deposition within a single cell of an example test cell 200, which may be part of a larger test array configuration. In this embodiment, drops of solvent 220 and 250 are deposited in both reference region 230 and measurement region 240. The composition and concentrations of solvent drops 220 and 250 may vary depending on the test situation. For example, they may be the same concentrations and closely matched in composition, or solvent drop 250 may be the same concentration as the solvent in target/solvent drop 260, with drops 220 both at the same concentration and composition. Additionally, a drop of target/solvent 260 is deposited within measurement region 240. Both reference region 230 and measurement region 240 reside within thermal isolation region 210. Drop size may range from approximately 100 pL to approximately 100 µL. For the purposes of use with this embodiment of the nanocalorimeter, drop size is approximately 100 pL to 1 µL.

Figure 3:
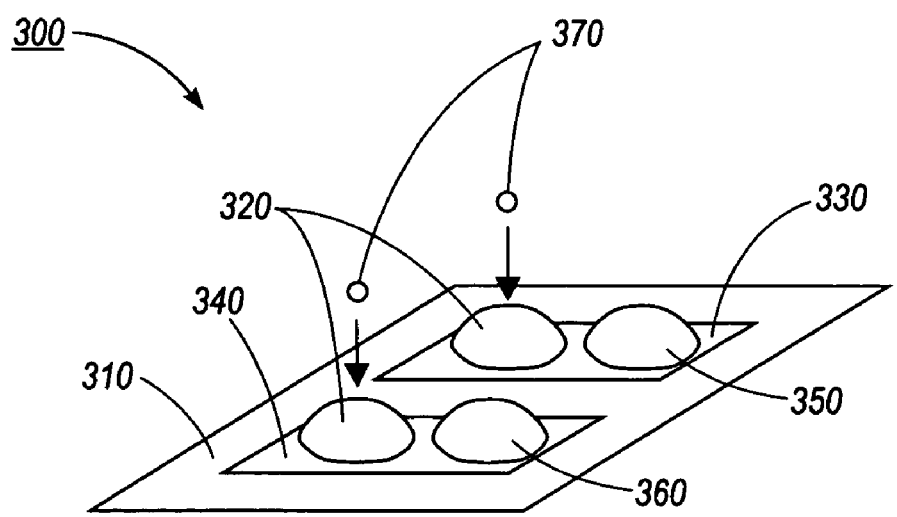
FIG. 3 is an illustration depicting deposition of the library compound on a single cell of a testing array, according to the embodiment of FIG. 2.

Drops of concentrated library compound 370 are then deposited on solvent drops 320, as illustrated in FIG. 3 with example test cell 300. For the purposes of this embodiment, the library compound has a concentration of 0.1 to 10 millimolar within a solvent, which is typically 50%-100% DMSO (dimethyl sulfoxide). Here combined solvent and library compound drops are located within reference region 330 and measurement region 340, both of which are situated within thermal isolation region 310. After concentrated library compound drops 370 are deposited, sufficient time is allotted to permit the test compound to diffuse and mix. After the library compound has mixed within the solvent, target/solvent drop 360 and solvent drop 350 are each merged with their respective library compound/solvent drops by any known means that does not introduce significant differential heating between the measurement and reference sides, such as, for example, that described in, U.S. application Ser. No. 10/115, 336, "Apparatus and Method for Using Electrostatic Force to Cause Fluid Movement", and measurements are performed to detect a heat of reaction in the measurement region, which is compared to the measurement taken for the combination of the library compound/solvent drop and reference solvent drop in the reference region.

In the case of the embodiment in FIG. 1, the bridge measurement directly senses the difference in heat evolved in the measurement and reference regions, eliminating the need for a post-measurement comparison of the two. Although for the purposes of this embodiment target and solvent are mixed on the test device, it will be appreciated by those skilled in the art that the target and solvent may be pre-mixed and deposited on the test device, which is fully contemplated by the specification and scope of the claims herein.

Figure 4:
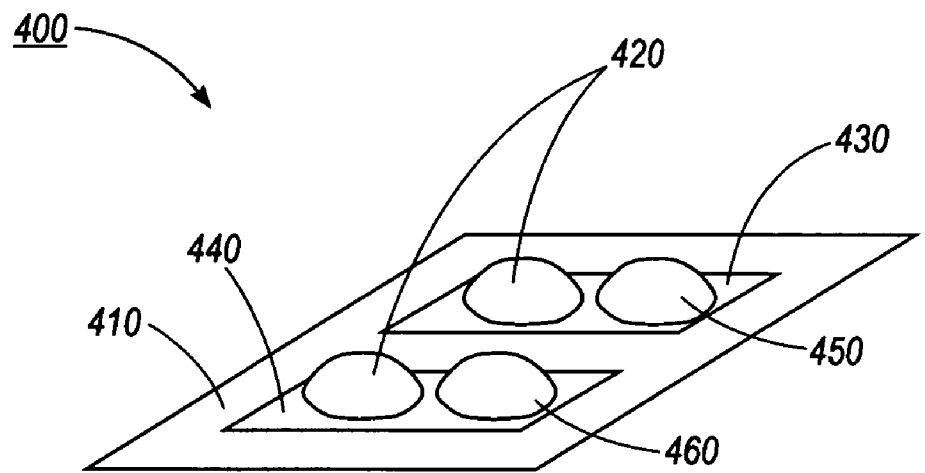
FIG. 4 is an illustration depicting solvent, modified solvent, and target drop deposition within a single cell of a testing array according to another embodiment of the method.

Turning now to FIG. 4, shown is an illustration of another embodiment depicting solvent and target drop deposition within a single cell of a testing array. Measurement region 440 and reference region 430 reside within thermal isolation region 410. During operation, a modified solvent 450 is deposited in reference region 430, and an unmodified solvent 420 is deposited within reference region 430 and measurement region 440. Modified solvent 450 is designed to accommodate the change in the unmodified solvent 420 after the addition of concentrated library compound 570 to obtain a better match of the final solvent conditions between the final test compound drop and target drop and the final test compound and reference solvent drop. Specifically, the modified solvent 450 will be created by combining the solvent 420 with the amount of different solvent contained in the library compound 570. A drop of target compound in a solvent solution 460 is deposited within measurement region 440. To eliminate heat of mixing between the solvent resulting from mixing the library compound 570 and the unmodified solvent 420 and the solvent in the target drop, solvent 460 is identical to the modified solvent 450. Consequently, the solvent in all four drops should be nearly identical after the addition of the concentrated library compound 570.

Figure 5:
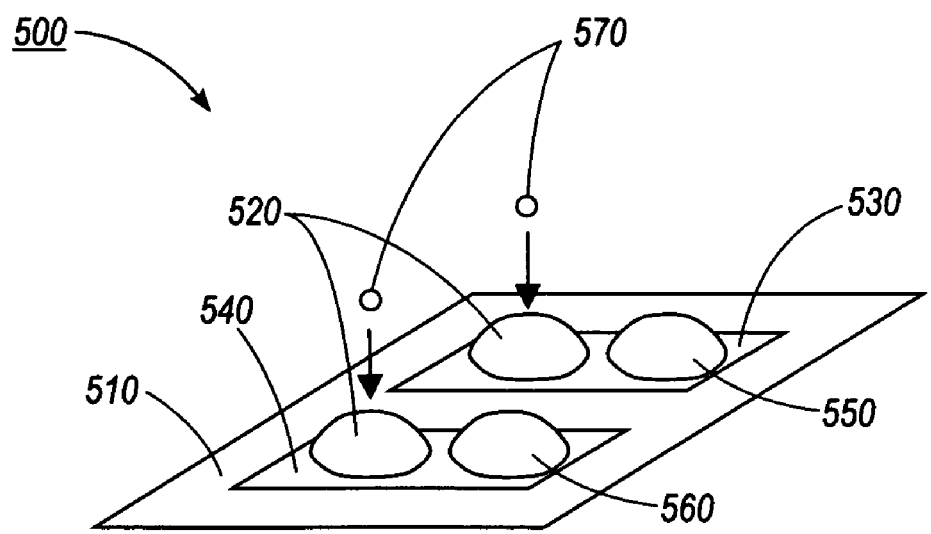
FIG. 5 is an illustration depicting deposition library compound on a single cell of a testing array, according to the embodiment of FIG. 4.

Drops of concentrated library compound 570 are then deposited on unmodified solvent drops 520, as illustrated in FIG. 5 with example test cell 500. The concentrated library compound 570 has sufficient to time to diffuse, as the remaining cells in the array are being prepared or another such array is being measured. As indicated in FIG. 5, drops of concentrated library compound are diffusing within modified solvent 520, located within reference region 530 and measurement region 540, which are located within thermal isolation region 510. For the purposes of this embodiment, the library compound has a concentration of 0.1 to 10 millimolar within a solvent, which is typically 50%-100% DMSO (dimethyl sulfoxide). Because the compound storage concentration is typically 100 times the concentration needed in the assay screening, the compound solvent is diluted substantially (100:1 to 10,000:1 depending on concentration of stored material) in the mixing step so the solvents in the two drops differ by at most 1%.

After concentrated library compound drops 570 are deposited, sufficient time is allotted to permit the test compound to diffuse or mix. After the library compound has mixed within the solvent, target/solvent drop 560 and modified solvent drop 550 are merged with their respective library compound/solvent drop by any known means and measurements are performed to detect a heat of reaction in the measurement region, which is compared to the measurement taken for the combination of the library compound/solvent drop and reference solvent drop in the reference region. This simplified approach is an improvement over operation of the nanocalorimeter disclosed in U.S. application Ser. No. 10/114,611, "Apparatus and Method for a Nanocalorimeter for Detecting Chemical Reactions", incorporated hereinabove. This improved approach eliminates an intermediate mixing step of library compounds with solvent that would have been required prior to introducing the compound library to the measurement instrument. With this method, the compound library can be introduced in the same concentration and in the same solvent that is used for storage.

Figure 6:
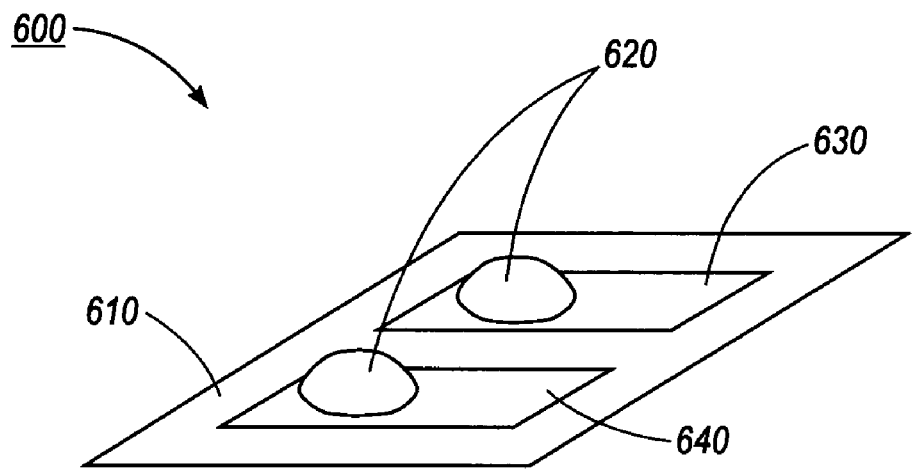
FIG. 6 is an illustration depicting library compound drop deposition within a single cell of a testing array.

Turning now to FIG. 6, there is illustrated another embodiment of the method herein, involving library compound drop deposition within a single cell of an example testing cell 600, which may be part of a larger test array configuration. In this embodiment, drops of library compound 620 are deposited in both reference region 630 and measurement region 640. For the purposes of this embodiment, the library compound has a concentration of 100 micromolar to 10 millimolar within a solvent, which is typically 50%-100% DMSO (dimethyl sulfoxide). Both reference region 630 and measurement region 640 reside within thermal isolation region 610.

Figure 7:
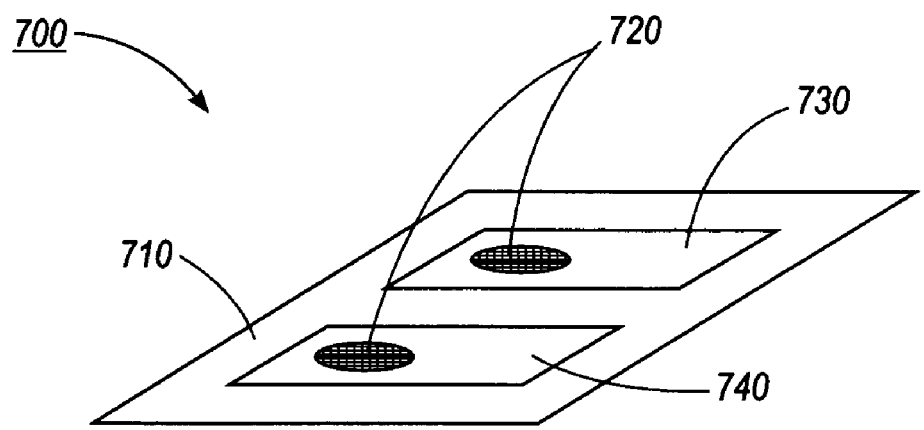
FIG. 7 is an illustration depicting drying of the library compound deposited on a single cell of a testing array.

The drops of library compound are then dried, as illustrated in FIG. 7 with example test cell 700. Here dried library compound drops 720 are located within reference region 730 and measurement region 440, both of which are situated within thermal isolation region 710. The ligand library molecules are robust and the solvent commonly used, DMSO, is quite volatile so the drops could be dried by several methods. For example, the drops may be dried at ambient temperature in a laminar flow of clean air, e.g., HEPA-filtered air, in a HEPA-filtered oven at room or elevated temperature, under vacuum, or at any other conditions that allow for removal of solvent and co-solvent. The filtered air is used to prevent contamination, but in cases where contamination is not a concern, filtering is not required. If the drops were dispensed at the storage concentrations in order to eliminate intermediate dilution steps, then because the storage concentrations are often very high such as 10 mM, the drops would be in very small volumes, such as 200 pL, which would dry quickly at ambient temperatures.

Figure 8:
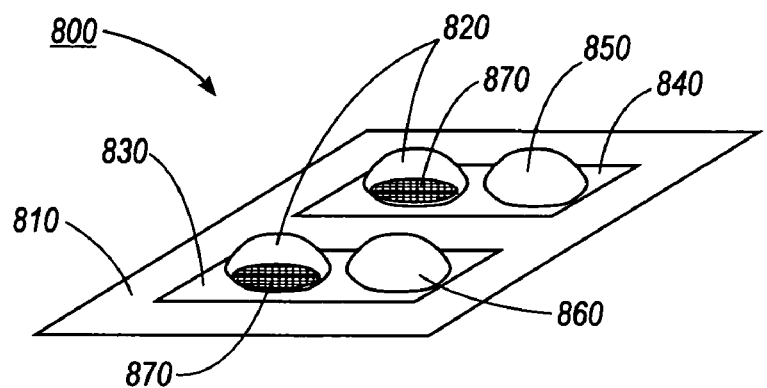
FIG. 8 is an illustration depicting solvent and target drop deposition within a single cell of a testing array according to the embodiment of FIG. 7.

Turning now to FIG. 8, shown is an illustration depicting solvent and target drop deposition within a single cell of a testing array. Measurement region 830 and reference region 840 reside within thermal isolation region 810. During operation, solvent 820 used to dissolve the library compounds has been deposited on the predeposited, dried library compound 870 in both the measurement region 830 and the reference region 840. Reference solvent 850 is also deposited in reference region 840. The reference solvent is similar to the solvent in drops 820 that dissolve the dried library compounds. The target material in a solvent solution 860 is deposited in measurement region 830. The solvent solution is identical to the solvent solutions 850 and 820. Since all the solvent solutions are identical, no heat of mixture will result from mixing the drops. In addition, only two material sources are needed to load the arrays and these are the solvent used in 820 and 840 and the dissolved target material. This reduction in material sources enables faster dispensing. Dispensing the library compound and storing it in dried form prior to dispensing the solvents can enable multiple arrays to be deposited with the same library compound combinations, which would reduce the amount of library material lost as dead volume or unused in the dispensing equipment.

Figure 9:
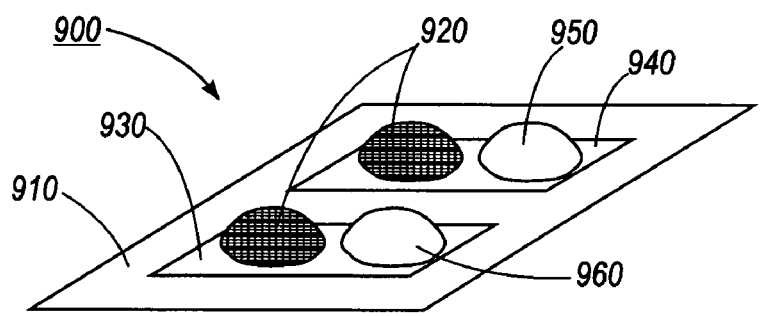
FIG. 9 is an illustration depicting dissolution of dried library compound by deposited solvent.

The pre-deposited dried library compound has sufficient time to dissolve, shown in FIG. 9, as the remaining cells in the array are being prepared or another such array is being measured. The use of a surface coating that minimizes the strength of the binding of the dried library to the detector surface may cause the dissolving of the dried library compound in the solvent 920 to proceed more expeditiously. Examples of such surface coatings include fluorocarbon and siloxane coatings. Other examples of coatings include patterned PEG (polyethylene glycol) coatings to minimize strong binding of, for example, peptides or proteins. In this example, the hydrophilic PEG coating is patterned to cover only a small area where the library compound is deposited, in order to maintain the hydrophobic character of the remaining surface area as needed for drop merging as described in, U.S. application Ser. No. 10/115,336, "Apparatus and Method for Using Electrostatic Force to Cause Fluid Movement". When the dried material is re-dissolved in a solvent drop, the drop covers an area larger than the patterned PEG, assuring that the border of the drop is on the hydrophobic coating. In addition to conventional hydrophobic surfaces, other examples of suitable surfaces include nano-textured coatings, such as nano-hairs that may be solution-coated onto surfaces. Commercially available nano-textured coatings include Nano-PEL™ coatings (Nano-Tex).

Alternatively, the pre-deposited dried library compounds can be prepared by commercially available technologies. As an example, Caliper Technologies offers its LibraryCard Reagent Array technology as a means to create arrays with spotted, dried library compounds for other companies to use in assays. According to Caliper Technologies, the dried reagents prepared using their technology readily redisperse in solvent.

As indicated in FIG. 9, solvent is dissolving library compound 920, located within reference region 940 and measurement region 930, which are located within thermal isolation region 910. Because the solvent being used to dissolve the library compound is the same for both drops of dried compound and for the drops, 850 and 860, and because the library compound is at sufficiently low concentration, no significant heat of mixing occurs. This simplified approach is an improvement over operation of the nanocalorimeter disclosed in U.S. application Ser. No. 10/114,611, "Apparatus and Method for a Nanocalorimeter for Detecting Chemical Reactions", incorporated hereinabove. This improved approach eliminates an intermediate mixing step and simplifies drop dispensing as required in the earlier application to avoid an introduced heat of mixing that could obscure the heat of reaction desired to be measured.

Figure 10:
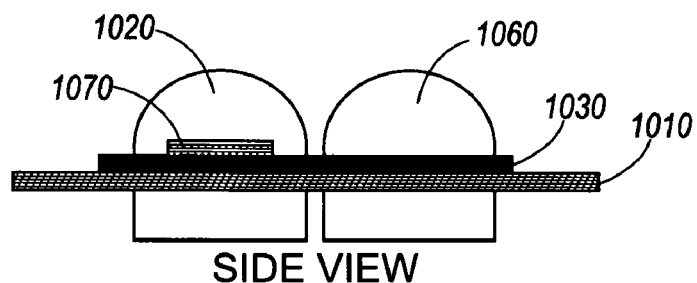
FIG. 10 is an illustration showing the side view of solvent and target drop deposition according to FIG. 8.

Drop deposition is illustrated in a side view in FIG. 10, in which thermal isolation region 1010 and measurement region 1030 are shown in profile. For the purposes of clarity, the library compound/solvent drop and reference solvent drop deposited within the reference region are not shown in this figure. Solvent drop 1020, which may be a 1%-4% DMSO solution, is deposited on predeposited and dried library compound 1070. Target compound and solvent drop 1060 has also been deposited in measurement region 1030. After the library compound has dissolved in the applied solvent, target/solvent drop 1060 and library compound/solvent drop 1020 are merged by any known means and measurements are performed to detect a heat of reaction, which is compared to the measurement taken for the combination of the library compound/solvent drop and reference solvent drop in the reference region. If the library compound reacts with the target compound, the heat of reaction dissipated in the measurement region will cause the temperature in that region to exceed the temperature of the reference region where no binding reaction occurs. The temperature change denotes that the reaction has occurred. The enthalpy of the reaction can be derived from this temperature change.

Figure 11:
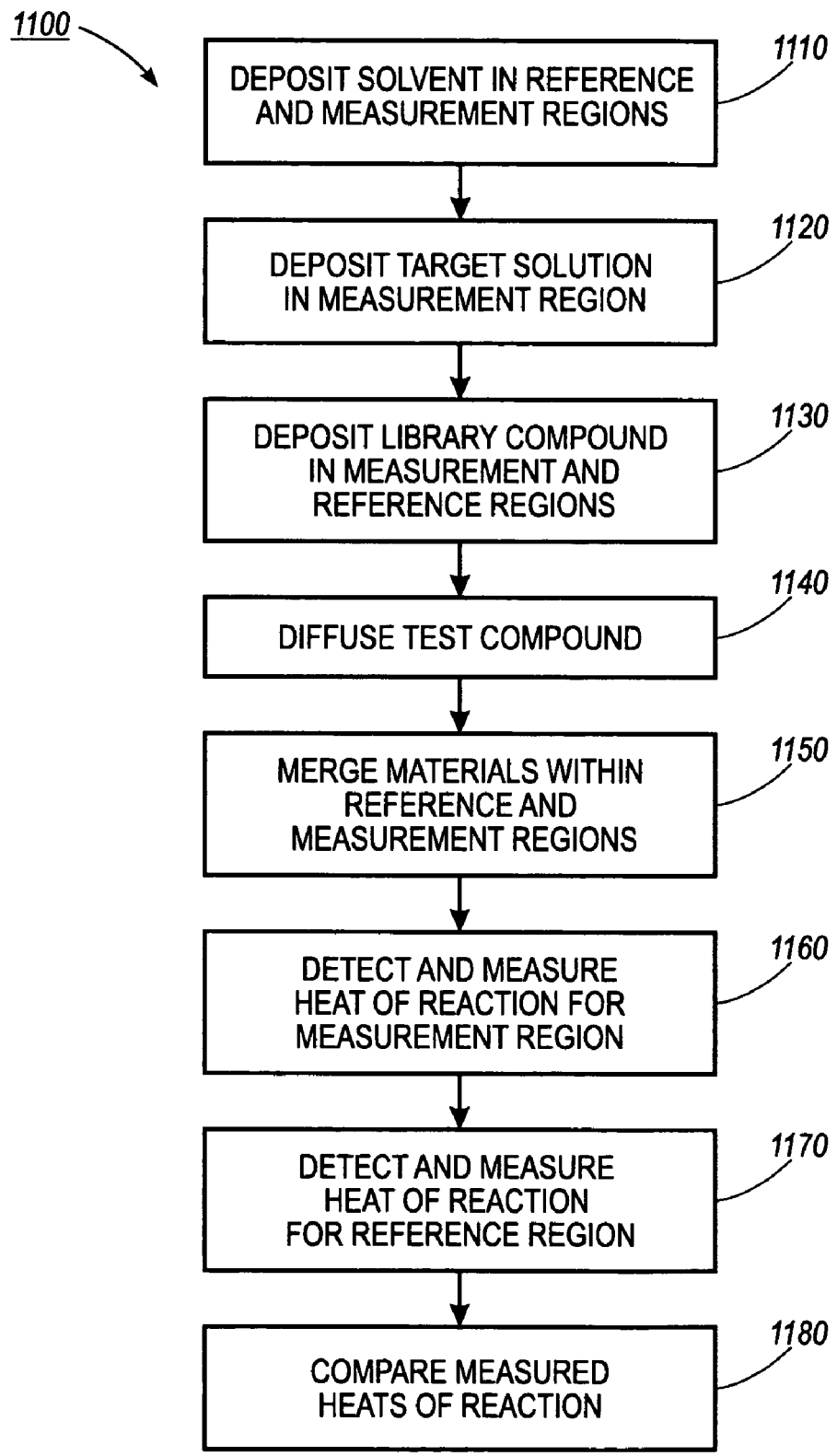
FIG. 11 is a diagram illustrating one embodiment of the method herein.

Turning now to FIG. 11, an embodiment of the subject method is summarized in a diagram. Here method 1100 includes deposition of solvent in the reference and measurement regions of a nanocalorimeter 1110, as described hereinabove. The solvent may be in the form of drops, with not less than one drop being deposited in each of the regions. As was discussed with reference to earlier embodiments herein, the solvent may be in either a modified or unmodified form and multiple drops of solvent may be deposited in the reference or measurement regions. At 1120, target is deposited in the measurement region of the nanocalorimeter. The target is contained in solvent, which may be in either a modified or unmodified form. Library compound is deposited in the measurement and reference regions at 1130. The library compound may be in the form of drops or may be in the form of dried compound as described with reference to FIGS. 7-9 hereinabove. In the embodiment in which the library compound is in the dried form, the dried library compound will be present in the measurement and reference regions prior to deposition of the solvent. A test compound is developed at 1140, with the test compound including the dried library compound dissolved in solvent or a concentrated library compound diffused in solvent. The materials within the reference region and measurement region are respectively merged at 1150. The materials within the reference region include the test compound and reference solvent; the materials within the measurement region include the test compound and the target in solvent. The heat of reaction for the measurement region is detected and measured at 1160, while the heat of reaction for the reference region may be simultaneously detected and measured at 1170. These heats of reaction are compared at 1180 to determine if a reaction has occurred between the ligand target and the library compound.

As will be appreciated, the method disclosed herein reduces or eliminates errors related to the heats of mixture, reduces the number of drops that need to be dispensed, reduces the number of different materials in drops that need to be dispensed, eliminates the need to separately deliver the library to the instrument, reduces the amount of material lost to dead volume in the dispensing tool, and enables the library to be captured more efficiently and separately prior to measurement.

While the present discussion has been illustrated and described with reference to specific embodiments, further modification and improvements will occur to those skilled in the art. For example, some targets can be applied and dried in a manner similar to the compound library. These are targets that do not require specific solvents to maintain specific conformations to remain active. Another modification would be to deposit target drops in both the reference and measurement regions and a single compound library drop in the measurement region with a solvent drop in the reference region. In this case target compounds will be mixed with solvent in the reference region and with compound library in the measurement region. Another modification is to not use a reference region in situations where the heat released is large and extends for a period of time longer than the merging transients. Reactions like strong enzyme reactions could be measured without a reference region. It is to be understood, therefore, that this disclosure is not limited to the particular forms illustrated and that it is intended in the appended claims to embrace all alternatives, modifications, and variations which do not depart from the spirit and scope of the embodiments described herein.

The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others.

What is claimed is:

1. A method for high-throughput screening assay sample preparation and testing for identification of binding between target compounds and library compounds, for use with a device measuring the enthalpy of reaction for such binding, comprising:

introducing not less than one selected library compound solution to a first solvent solution on the device such that they mix to form not less than one library compound/solvent solution;

introducing not less than one target compound/second solvent solution on the device;

establishing thermal equilibrium of the device;

merging said not less than one library compound/solvent solution with said target compound/solvent solution at not less than one first location on the device;

merging said not less than one library compound/solvent solution with a third solvent solution at not less than one second location on the device;

detecting a first heat of reaction for said merged library compound/solvent solution and said target compound/solvent solution;

detecting a second heat of reaction for said merged library compound/solvent solution with said third solvent solution;

comparing said first and second heats of reaction; and detecting a binding operation has occurred between said merged library compound/solvent solution and said target compound/solvent solution, when the comparing step finds the first heat of reaction is greater than the second heat of reaction.

2. The method for high-throughput screening assay sample preparation and testing according to claim 1, wherein said first solvent, said second solvent and said third solvent solutions are at approximately the same co-solvent concentration.

3. The method for high-throughput screening assay sample preparation and testing according to claim 1, wherein said second solvent solution and said third solvent solution are at a second concentration and said first solvent solution is at a first concentration.

4. The method for high-throughput screening assay sample preparation and testing according to claim 1, wherein said selected library compound is concentrated within a solution, said concentration having a range, wherein said range is approximately 100 micromolar to 10 millimolar concentration.

5. The method for high-throughput screening assay sample preparation and testing according to claim 1, wherein said first solvent solution comprises an unmodified solvent solution.

6. The method for high-throughput screening assay sample preparation and testing according to claim 1, wherein said second solvent solution and said third solvent solution comprise a modified solvent solution.

7. The method for high-throughput screening assay sample preparation and testing according to claim 1, wherein said library compound comprises a dried library compound material.

8. The method for high-throughput screening assay sample preparation and testing according to claim 7, wherein said dried library compound is dissolved in a solvent solution prior to merging with said target compound/solvent solution.

9. The method for high-throughput screening assay sample preparation and testing according to claim 1, wherein merging comprises application of electrostatic force.

10. The method for high-throughput screening assay sample preparation and testing according to claim 1, wherein said not less than one target compound comprises dried target compound material.

11. The method for high-throughput screening assay sample preparation and testing according to claim 4, wherein said library compound solution includes one or more co-solvents, wherein said co-solvent is present in a concentration ranging from approximately 0.1% to approximately 100%.

12. The method for high-throughput screening assay sample preparation and testing according to claim 11, wherein said co-solvent present in said library compound solution comprises dimethyl sulfoxide, and wherein said dimethyl sulfoxide is present in a concentration ranging from approximately 50% to approximately 100%.

13. The method for high-throughput screening assay sample preparation and testing according to claim 7; wherein said library compound/solvent material is dried at ambient temperature in a laminar flow of filtered air.

14. The method for high-throughput screening assay sample preparation and testing according to claim 1, wherein said first solvent solution further includes target compounds.

15. The method for high-throughput screening assay sample preparation and testing according to claim 1, wherein said target compound and second solvent are introduced separately on the device and mix on the surface of the device to form said target compound/solvent solution.

16. The method for high-throughput screening assay sample preparation and testing according to claim 1, wherein the calorimetric device is a nanocalorimetric device.

17. The method for high-throughput screening assay sample preparation and testing according to claim 1, wherein merging comprises application of electrical force.

18. A method for high-throughput screening assay sample preparation and analysis for identification of binding between target compounds and library compounds for use within a nanocalorimeter, wherein said nanocalorimeter includes thermal isolation regions, reference regions, and measurement regions, the method comprising:
  depositing not less than one drop of a first solvent solution within each of not less than one reference region and not less than one measurement region;
  depositing not less than one drop of a second solvent solution within each of not less than one measurement region and not less than one reference region;
  depositing not less than one drop of target compound within the measurement region, such that said not less than one drop of target compound contacts and mixes with said not less than one drop of second solvent solution to form a target compound/solvent solution;
  depositing not less than one drop of selected library compound solution in the not less than one measurement region and the not less than one reference region, such that said not less than one drop of selected library compound contacts and mixes with said not less than one drop of first solvent solution to form a library compound/solvent solution;
  establishing thermal equilibrium of the not less than one measurement region and the not less than one reference region;
  merging said library compound/solvent solution with said second solvent solution within the not less than one reference region;
  merging said library compound/solvent solution with said target compound/solvent solution within the not less than one measurement region;
  detecting a first heat of reaction for said merged library compound/solvent solution and said target compound/solvent solution within the not less than one measurement region;
  detecting a second heat of reaction for said merged library compound/solvent solution and said second solvent solution within the not less than one reference region;
  comparing said heats of reaction for the not less than one reference region and the not less than one measurement region; and
  detecting a binding operation has occurred between said merged library compound/solvent solution and said target compound/solvent solution, when the comparing step finds the first heat of reaction is greater than the second heat of reaction.

19. The method for high-throughput screening assay sample preparation according to claim 18, wherein said deposited drops have a size, said size ranging from approximately 10 nL to in excess of 10 μL.

20. The method for high-throughput screening assay sample preparation according to claim 18, wherein said deposited drops have a size, said size ranging from approximately 200 nL to approximately 400 nL.

21. The method for high-throughput screening assay sample preparation according to claim 18, wherein said second solvent comprises a modified solvent.

22. The method for high-throughput screening assay sample preparation according to claim 18, further comprising depositing two drops of said solvent within said reference region.

23. The method for high-throughput screening assay sample preparation according to claim 18, wherein said library compound is in a dried form.

24. The method for high-throughput screening assay sample preparation according to claim 23, wherein mixing said test compound comprises dissolving said dried library compound within said first solvent.

25. The method for high-throughput screening assay sample preparation according to claim 18, wherein said first solvent and said second solvent are at approximately the same solvent concentrations.

26. The method for high-throughput screening assay sample preparation according to claim 18, wherein said first solvent solution and said second solvent solution are at differing solvent concentrations.

27. The method for high-throughput screening assay sample preparation according to claim 18, wherein said second solvent solution is a modified solvent solution and said first solvent solution is an unmodified solvent solution.

28. The method for high-throughput screening assay sample preparation according to claim 18, wherein merging comprises application of electrostatic force.

29. The method for high-throughput screening assay sample preparation according to claim 18, further comprising mixing said target compound and said second solvent mixed prior to deposition on the device.

30. A method for high-throughput screening assay sample preparation and analysis for use within a nanocalorimeter, wherein said nanocalorimeter includes thermal isolation regions and measurement regions, the method comprising:
  depositing not less than one drop of target material within the measurement region;
  depositing not less than one drop of selected library compound solution in the not less than one measurement region;
  establishing thermal equilibrium within the regions of the nanocalorimeter;

merging said library compound solution with said target material solution within the not less than one measurement region;

detecting a heat of reaction for said merged library compound solution and said target material solution within the not less than one measurement region when said detecting of the heat of reaction extends for a period of time longer than a time of merging transients;

measuring said heat of reaction for the not less than one measurement region; and determining a binding operation has occurred when the heat of reaction is has been detected and measured.

31. A method for high-throughput screening assay sample preparation and analysis for identification of binding between target compounds and library compounds for use with a device measuring the enthalpy of reaction for such binding, the device having thermal isolation regions, reference regions, and measurement regions, the method comprising:

depositing not less than one drop of a first solvent solution within each of not less than one reference region and not less than one measurement region;

depositing not less than one drop of a second solvent solution within each of not less than one measurement region and not less than one reference region;

depositing not less than one drop of target compound within the measurement region, such that said not less than one drop of target compound contacts and mixes with said not less than one drop of second solvent solution, to form a target compound/solvent solution;

depositing not less than one drop of selected library compound solution in the not less than one measurement region and the not less than one reference region, such that said not less than one drop of selected library compound contacts and mixes with said not less than one drop of first solvent solution to form a library compound/solvent solution;

establishing thermal equilibrium of the not less than one measurement region and the not less than one reference region;

merging said library compound/solvent solution with said second solvent solution within the not less than one reference region;

merging said library compound/solvent solution with said target compound/solvent solution within the not less than one measurement region;

detecting a first heat of reaction for said merged library compound/solvent solution and said target compound/solvent solution within the not less than one measurement region;

detecting a second heat of reaction for said merged library compound/solvent solution and said second solvent solution within the not less than one reference region;

comparing said heats of reaction for the not less than one reference region and the not less than one measurement region; and detecting a binding operation has occurred between said merged library compound/solvent solution and said target compound/solvent solution, when the comparing step finds the first heat of reaction is greater than the second heat of reaction.

* * * * *